United States Patent [19]

El-Antably

[11] 4,031,218

[45] June 21, 1977

[54] 7-(2,3-DIHYDROXYPROPYL-1,3-DI-N-PROPYLXANTHINE AND A PHARMACEUTICAL COMPOSITION CONTAINING SAME USEFUL AS A BRONCHIAL MUSCLE RELAXANT

[75] Inventor: Samir M. El-Antably, St. Ann, Mo.

[73] Assignee: Mallinckrodt, Inc., St. Louis, Mo.

[22] Filed: Apr. 28, 1976

[21] Appl. No.: 680,936

[52] U.S. Cl. .............................. 424/253; 260/256
[51] Int. Cl.² ................ A61K 31/52; C07D 473/04
[58] Field of Search ................... 424/253; 260/256

[56] References Cited

UNITED STATES PATENTS

| | | | |
|---|---|---|---|
| 2,517,410 | 8/1950 | Papesch | 260/256 |
| 2,756,229 | 7/1956 | Stoll et al. | 260/256 |

*Primary Examiner*—Albert T. Meyers
*Assistant Examiner*—Daren M. Stephens
*Attorney, Agent, or Firm*—R. J. Klostermann

[57] ABSTRACT

7-(2,3-dihydroxypropyl)-1,3-di-n-propylxanthine is comparable to theophylline as a bronchodilator but less active in regard to undesired side effects.

3 Claims, No Drawings

7-(2,3-DIHYDROXYPROPYL-1,3-DI-N-PROPYLXANTHINE AND A PHARMACEUTICAL COMPOSITION CONTAINING SAME USEFUL AS A BRONCHIAL MUSCLE RELAXANT

BACKGROUND OF THE INVENTION

1. Field of the Invention

This invention relates to 7-(2,3-dihydroxypropyl)-1,3-di-n-propylxanthine, its use as a bronchodilator, i.e., a bronchial muscle relaxant and to pharmaceutical compositions containing it.

2. Description of the Prior Art

Theophylline (1,3-dimethylxanthine) represented by the following structure

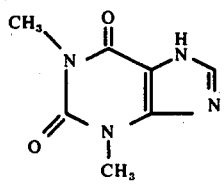

I is a naturally occurring xanthine alkaloid which was first reported as a therapeutic agent in asthma nearly 55 years ago. Its use as an oral bronchodilator did not become popular until the late 1930's. It was soon learned, however, that although theophylline was effective, its lack of water solubility and ability to produce undesirable side effects detracted from its usefulness. Consequently, continual effort was directed toward improving the water solubility of theophylline as well as toward synthesizing various derivatives in an attempt to increase safety while retaining the desirable pharmacological characteristics.

Solubilization of theophylline has been achieved by forming addition compounds like theophylline ethylenediamine (aminophylline), salts such as choline theophyllinate (oxtriphylline), or combinations with sodium acetate or sodium glycinate. Unfortunately, these "soluble" theophylline preparations have not served to appreciably reduce the incidence of undesirable effects on the gastrointestinal, cardiovascular, renal, and central nervous systems.

Attempts to modify the chemical structure of theophylline to obtain a compound with greater bronchodilator selectively has not met with measurable success. Compounds with increased bronchodilator potency have been made but at the expense of decreased tolerance. The only synthetic derivative of theophylline that has gained any degree of therapeutic acceptance is dyphylline, 7-(2,3-dihydroxypropyl) 1,3-dimethylxanthine represented by the following formula.

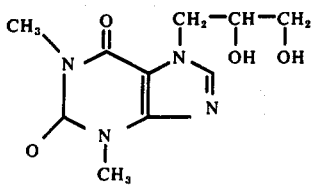

II

Dyphylline possesses inherent high water solubility and few of the usual theophylline-like side effects; however, it also possesses less bronchodilator potency than theophylline.

It is apparent from the effects of dyphylline that 1,3-dihydroxypropyl substitution at position 7 of the basic theophylline molecule markedly decreases overall potency, in regard to both therapeutic and side effects. Roth et al. (J. Pharmacol, Exp. Ther. 121:487, 1957) observed this same phenomenon with 7-β-hydroxypropyl-1,3-dimethylxanthine as did Armitage et al. (Brit. J. Pharmacol. 17:196, 1961) with a series of 7-hydroxyalkyl-6-thioxanthines. From the reports of Roth et al. and McColl et al. (J. Pharmacol. Exp. Ther. 116:343, 1956), it is shown that 7-dihydroxypropyl substitution decreases activity more than 7-monohydroxypropyl substitution.

On the other hand, various investigators have found that the pharmacologic activity of theophylline can be increased by dialkyl substitution at positions 1 and 3. Kattus et al. (Bull. John Hopkins Hosp. 89:1-8, 1951) demonstrated that 1,3-diethyl, 1,3-dipropyl, and 1,3-dibutyl xanthine exhibited extremely potent diuretic and emetic properties. Unfortunately, bronchodilator action was not assessed. Armitage et al. evaluated an entire series of 1,3-dialkyl substituted 6-thioxanthines. Most of the compounds tested, including the 1,3-dipropyl derivative, possessed potent bronchodilator activity and were potent emetic agents.

It would appear, therefore, from these literature reports that neither 7-hydroxyalkyl nor 1,3-dialkyl substitution of theophylline alone serves to better the therapeutic efficacy of the molecule as a bronchodilator. The former decreases side-effects at the expense of potency and the latter increases potency at the expense of tolerance.

U.S. Pat. No. 2,756,229 discloses a series of substituted theophyllines having both 7-monohydroxyalkyl and 1,3-dialkyl substituents. Specially disclosed are those compounds represented by Formulae III and IV.

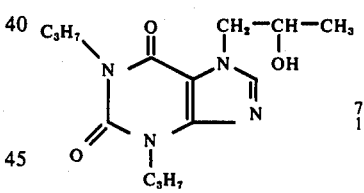

III 7-(2-Hydroxypropyl)-1,3-di-n-propylxanthine

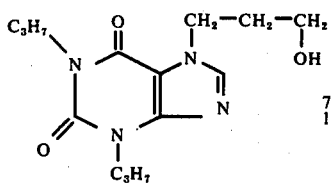

IV 7-(3-Hydroxypropyl)-1,3-di-n-propylxanthine

The are claimed by the patentee to be strong diuretics in comparison with theophylline and at the same time are said to be well tolerated. Nothing is disclosed about their bronchodilator properties.

Applicant has found that although Compounds III and IV are more potent bronchodilators than theophylline they are therapeutically undesirable because of increased undesirable emetic, cardiovascular and central nervous system (CNS) effects.

Accordingly, a compound comparable to theophylline as a bronchodilator, but having reduced adverse side effects and increased water solubility would be an advancement in the art.

BRIEF DESCRIPTION OF THE INVENTION

In accordance with this invention there is provided the compound 7-(2,3-dihydroxypropyl)-1,3-di-n-propylxanthine (represented by Formula V) which has bronchodilator properties comparable to theophylline and also less adverse side effects.

$$\text{n-C}_3\text{H}_7\text{-N-C(=O)-N(n-C}_3\text{H}_7\text{)-C(=O)-C=C-N(CH}_2\text{CHOHCH}_2\text{OH)-CH=N}$$ (V)

On a molar basis, the compound of this invention is comparable to theophylline as a bronchodilator but less active in regard to acute toxicity as well as undesirable cardiovascular, CNS, diuretic and oral emetic effects. Additionally, it is considerably more water soluble than theophylline.

Another aspect of this invention is directed to a pharmaceutical composition containing a therapeutically effective amount of the above mentioned compound in a pharmaceutically acceptable carrier.

Another aspect of this invention is directed to a method for the treatment of reversible airway obstruction due to bronchoconstriction which comprises administering to a living animal body suffering from such condition a therapeutically effective amount of the compound of this invention.

DETAILED DESCRIPTION OF INVENTION

The compound of this invention 7-(2,3-dihydroxypropyl)-1,3-di-n-propylxanthine (V) may be prepared using the reactions diagrammed below:

$$\text{CH}_3\text{.CH}_2\text{CH}_2\text{—N=C=O + CH}_3\text{CH}_2\text{CH}_2\text{NH}_2 \rightarrow \text{1,3-di-n-propyl urea}$$ (VI)

$$\text{VI + H}_2\text{C(COOH)}_2 \rightarrow \text{1,3-di-n-propylbarbituric acid}$$ (VII)

$$\text{VII + POCl}_3 \rightarrow \text{1,3-di-n-propyl-4-chlorouracil}$$ (VIII)

$$\text{VIII + H}_2\text{NCH}_3 \rightarrow \text{1,3-di-n-propyl-4-methylaminouracil}$$ (IX)

$$\text{IX + Isoamylnitrite} \rightarrow \text{1,3-di-n-propylxanthine}$$ (X)

$$\text{X + ClCH}_2\text{CHOHCH}_2\text{OH} \rightarrow \text{7-(2,3-dihydroxypropyl)-1,3-di-n-propylxanthine}$$ (V)

EXAMPLE 1

The compound of this invention, 7-(2,3-dihydroxypropyl)-1,3-di-n-propylxanthine, was prepared as follows:

A. Synthesis of 1,3-di-n-propyl urea (VI)

1700 g. (98.4%) of product was prepared according to the method of Hayes et al., J. Agr. Food Chem. 17, 1077 (1969) from n-propylisocyanate (1020 g. 12 mole) and n-propylamine (708 g., 4.75 mole).

B. Synthesis of 1,3-di-n-propylbarbituric Acid (VII)

Synthesis was carried out according to the procedure of Goldner, Ann. Chem., 691, 142 (1966) using 1,3-di-n-propylurea (777 g., 5.38 mole), malonic acid (660 g., 6.34 mole), glacial acetic acid (1050 ml.) and acetic anhydride (2160 ml.) to obtain 790 g. (69.2%) of product, melting point 77° – 80° C. NMR and IR spectra were consistent with the assigned structure.

Calc. for $C_{10}H_{16}N_2O_3$: C, 56.58; H, 7.59; N, 13.20. Found: C, 56.50; H, 7.66; N, 13.08.

C. Synthesis of 1,3-di-n-propyl-4-chlorouracil (VIII)

Synthesis was carried out according to the Goldner method using the 1,3-di-n-propylbarbituric acid (340 g., 1.6 mole) and phosphorous oxychloride (1920 ml.). The crude product was distilled at 135° – 145°/0.05 mm. to obtain pure VIII, 1400 g. (95.1%), melting point 64° – 67°. NMR spectra was consistent with the proposed structure.

D. Synthesis of 1,3-di-n-propyl-4-methylamino uracil (IX)

Preparation was carried out by slightly modifying the Goldner procedure. A solution of 1,3-di-n-propyl-4-chlorouracil (1400 g., 6.08 mole) in isopropyl alcohol (8l) was treated with a solution of monomethylamine (about 400 g.) in isopropanol (6l). The mixture was stirred overnight at room temperature. It was then evaporated to dryness, treated with excess water, filtered, resuspended in water, filtered and air dried to obtain pale white crystals melting point 108° – 110° C., 1240 g. (90.64%). IR and NMR spectra were consistent with the assigned structure.

Analysis for $C_{11}H_{19}N_3O_2$: Calculated For: C, 58.64; H, 8.50; N, 18.65. Found: C, 58.72; H, 8.41; N, 18.56.

E. Synthesis of 1,3-di-n-propylxanthine (X)

Synthesis was carried out according to the Goldner method using a solution of 1,3-di-n-propyl-4-methylaminouracil (690 g. 3.06 mole) in ethanol (5l), isoamylnitrite (655 g., 5.6 mole) and a saturated alcoholic hydrogen chloride solution (42 ml.). The product was obtained as pale white crystals, 470 g. (65%), melting point 201° – 205° C. IR and NMR spectra were consistent with the proposed structure.

F. Synthesis of 7-(2,3-dihydroxypropyl)-1,3-di-n-propylxanthine (V)

A suspension of 1,3-di-n-propylxanthine (250.1 g., 1.06 mole) in water (300 ml.) was treated with sodium hydroxide solution (50%, 85 ml.). The mixture was filtered, and evaporated to dryness. The residue obtained was treated with a solution of 1-chloro-2,3-dihydroxypropane (170 g., 1.59 mole) in isopropanol (700 ml.). The mixture was stirred at reflux overnight, filtered, and evaporated to dryness to obtain a brown gummy residue. This residue was dissolved in isopropyl alcohol, and stirred overnight with charcoal (20 gm.). The mixture was filtered, concentrated and allowed to crystallize over night at 0° to −5° C. The crystals were filtered, suspended in ether, refiltered and air dried to yield white crystals (224 g., 72.17%), melting point 88° – 91°. Tlc (5μl of a 5% solution) on a silica plate developed in chloroform:methanol (9.5:0.5) showed one spot. IR and NMR spectra were consistent with the proposed structure.

Analysis for $C_{14}H_{22}N_4O_4$: Calc. for: C, 54.18; H, 7.15; N, 18.05. Found: C, 54.39; H, 7.32; N, 18.03.

The solubility in water was 10% w/v and in chloroform about 31% (w/v).

The compound of this invention, 7-(2,3-dihydroxypropyl)-1,3-di-n-propylxanthine (V), theophylline (I), 7-(2-hydroxypropyl) 1,3-di-n-propylxanthine (III), 7-

(3-hydroxypropyl)-1,3-di-n-propylxanthine (IV) and dyphylline (II) were tested according to the test methods described below for their bronchodilator, acute toxicity, and side effect properties.

Results are given in Tables 1 and 2 below:

TEST METHODS

A. Compound Administration and Data Presentation

With the exception of theophylline, all compounds were administered as the free base dissolved or suspended in appropriate aqueous vehicles. Theophylline, because of its poor solubility, was administered in the form of aminophylline, its ethylenediamine addition compound. The ethylenediamine portion of the molecule is pharmacologically inert, but renders solubility and convenience of use (Simons et al., S. Med. Journ. 68:802, 1975). For the purpose of comparison, aminophylline was considered to contain 80% free theophylline by weight (Piafsky and Ogilvie, New England J. Med. 292: 1218, 1975). Final comparisons were always based on the calculated dose of theophylline. Because of obvious differences in molecular weights, all compounds were compared on a molar basis rather than on absolute weight.

B. Bronchodilator Studies in Guinea Pigs

1. Isolated Trachea Preparation

The in vitro bronchodilator activity of each compound was estimated on the spirally cut guinea pig tracheal strip preparation as described by Constantine, (J. Pharm. Pharmacol. 17:384, 1965). Large Camm English Short Hair male guinea pigs (800–1200 gm.) were employed in order to obtain three spiral tracheal strips from one animal. Strips were suspended in 50 ml. tissue baths containing modified Krebs-Henseleit solution at 38° C. and aerated with 95% $O_2$/5% $CO_2$. Pilocarpine HCl, 1 mg/liter, was added to the solution to maintain a sustained contraction and to promote rapid recovery of the muscle. A Grass FT 0.03 force displacement transducer was used to electronically record muscle response. Concentration-relaxation relationships were obtained for each compound by logarithmically increasing bath concentration until maximum (100%) relaxation was observed. Tissues were washed between doses and allowed 30 minutes to recover. Linear regression analysis of percent response vs. log of bath concentration allowed calculation of a slope and $EC_{50}$ value (concentration producing 50% of maximum relaxation) for each compound. Each dose of each compound was tested a minimum of six times.

2. Protection Against Histamine Aerosol

In vivo bronchodilator activity was estimated by measuring the ability of each compound to protect guinea pigs against the constricting bronchospasm induced by exposure to histamine as described by Armitage et al. (British J. Pharmacol. 16:59, 1961). Adult Camm English Short Hair male albino guinea pigs (270–600 gm.) were singularly confined in an inverted glass aquarium and continuously exposed to a finely atomized mist of 0.5% histamine diphosphate produced by a Devilbiss No. 40 nebulizer and compressed air at 300 mm. Hg. pressure. The period from the start of aerosolization until the appearance of ultimate collapse or convulsions is defined as the preconvulsive time and is relatively constant in the same animal. Preconvulsive times were determined for each dose of each compound in at least six guinea pigs. Control preconvulsive times were obtained three days prior to and three days following drug administration. Percent protection afforded by each compound was calculated by the formula:

$$\% \text{ Protection} = (1 - C/T) \times 100$$

where $C$ is the average control preconvulsive time and $T$ is the test preconvulsive time after compound administration, both in seconds. Animals with control preconvulsive times greater than 2 minutes were not used and if test preconvulsive time was longer than 10 minutes, 100% protection was arbitrarily assumed. The dose of each compound causing 50% protection ($PD_{50}$) was calculated by the method of Litchfield and Wilcoxon (J. Pharmacol. Exp. Ther. 96:99, 1949).

The $PD_{50}$ of each experimental compound was determined after both intraperitoneal and oral administration. A minimum of 3 dose levels and 6 animals per dose were employed to obtain meaningful dose-response data. Protection was assessed 15–20 minutes after intraperitoneal injection and 35–40 minutes after oral gavage with a flexible plastic tube. Animals were fasted overnight prior to oral dosing. All compounds were administered in aqueous solution in concentrations commensurate to a proper volume dose. Guinea pigs were utilized between 1 and 3 times but no animal received the same compound twice in succession with a minimum of 3 days rest between doses.

C. Acute Toxicity Studies

1. Intravenous and Oral $LD_{50}$ in Mice

The acute median lethal dose ($LD_{50}$) of each compound was determined in mice after both intravenous and oral administration. Swiss albino mice (Charles River) ranging in weight from 19.1 to 23.2 gm. were used. Sexes were equally represented in each dose group of at least six animals. Appropriate doses of each compound dissolved in distilled water were intravenously injected in the lateral tail vein at a rate of 1 ml./min. or orally administered via a feeding needle. Acute responses and lethalities were observed and respective $LD_{50}$ values were calculated according to the method of Litchfield and Wilcoxon (J. Pharmacol. Exp. Ther. 96:99, 1949).

2. Oral $LD_{50}$ in Guinea Pigs

The acute median lethal dose of each compound after oral administration was also determined in guinea pigs. Camm English Short Hair albino guinea pigs with sexes equally represented and ranging in weight from 255 to 311 gm. were used. A minimum of six animals per dose level were employed. Oral dosing was accomplished with a flexible tube inserted into the stomach. All guinea pigs were fasted overnight. Due to their low solubilities, it was necessary to suspend compounds III and IV in 0.5% methylcellulose. The other compounds were dissolved in distilled water. Following administration of the appropriate doses, acute responses and lethalities were observed and $LD_{50}$ values were calculated by the method of Litchfield and Wilcoxon (J. Pharmacol. Exp. Ther. 96:99, 1949).

D. Cardiovascular Studies

1. Dog Hind Limb Perfusion Preparation

A total of 12 adult mongrel dogs of either sex were used to assess the direct intra-arterial dilating capacity of the five experimental compounds. Animals were anesthetized with pentobarbital sodium, 30–35 mg/kg i.v., and surgically prepared to allow arterial blood flow into the femoral artery, and essentially the entire hind limb, to be controlled and held constant. This was accomplished with a Harvard Variable Speed Peristaltic Pump after proximal and distal cannualtion of the femoral artery. Changes in arterial vascular resistance were reflected as changes in perfusion pressure as measured from a T-tube on the distal side of the pump. Mean systemic arterial pressure was also recorded from the contralateral femoral artery. Drug solutions, dissolved in saline, were injected into the arterial blood supply immediately prior to entering the cannulated distal artery. Logarithmically increasing doses were given at 10-minute intervals and responses were recorded.

2. Isolated Rabbit Heart Preparation

In-vitro cardiodynamic activity of each compound except dyphylline was determined on the spontaneously beating isolated rabbit heart by the Langendorff method as modified by Anderson and Craver (J. Pharmacol. Exp. Ther., 93:135, 1948). After securing the extracted heart's ascending aorta to the apparatus, the coronaries were continuously perfused with aerated Chenoweth's solution (Chenoweth and Koelle, J. Lab. Clin. 31:600, 1946) maintained at a constant pressurehead and temperature of 38° C. The effects of logarithmically increasing doses of each compound were determined on contractile force, heart rate, and coronary flow. Drugs were dissolved in minimal volumes of Chenoweth's solution and injected into the downspout containing perfusate at 5–10 minute intervals.

3. Intravenous Cardiovascular Evaluation in Dogs

Thirteen adult mongrel dogs of either sex ranging in weight from 16.7 to 25.0 kg were employed to compare the overall intravenous cardiovascular activity of the five experimental compounds. Three dogs were utilized for each compund except for dyphylline (Compound II) which was tested in one animal.

Dogs were anesthetized with pentobarbital sodium, 30–35 mg/kg i.v., fitted with a cuffed endotracheal tube, and ventilated with a Harvard Animal Respiratory Pump. A femoral vein was cannulated for i.v. drug administration. The left common carotid artery was cannulated and the cannula tip advanced into the aortic arch. A median sternotomy was performed and appropriately sized electromagnetic blood flow transducers (Biotronex) were placed around the ascending aorta and left anterior descending coronary artery. These procedures allowed continuous recording or calculation of the following parameters:

a. Mean Arterial Pressure (MAP); from the aortic cannula.
b. Heart Rate (HR); electronically from pulsatile ascending aortic flow.
c. Cardiac Output (CO); mean ascending aortic flow.
d. Myocardial Contractile Force (MCF); dQ/dt, the first derivative of maximum aortic flow rate, also known as peak aortic flow acceleration.
e. Stroke Volume (SV); quotient of CO/HR.
f. Cardiac Work (CW); product of CO X MAP.
g. Total Peripheral Resistance (TPR); quotient of MAP/CO.
h. Coronary Flow (CF); mean left anterior descending (LAD) coronary flow.
i. Coronary Resistance (CR); quotient of MAP/CF.

Logarithmically increasing doses of the appropriate compound were injected at 20-minute intervals. Responses were measured at 1, 2, 5, 10, 15 and 20 minutes after each dose and the average response during that period was calculated. Theophylline (aminophylline), dyphylline (II), and Compound V were employed in both 20 and 80 mg/ml concentrations in distilled water. Compounds III and IV were used in 10 and 30 mg/ml concentrations respectively.

E. Emetic Studies in Dogs

1. Intravenous $ED_{50}$

Twelve adult mongrel dogs of either sex were employed to determine the median emetic dose ($ED_{50}$) of all five experimental compounds after intravenous administration. Appropriate doses of each compound were injected to groups of 4 animals and they were observed for emesis and signs of CNS stimulation. Onset, frequency, and duration of emetic episodes were also recorded. The dogs were not fasted, were allowed at least 2 days rest between doses, and no animal received the same compound twice in succession. Previous studies have shown this protocol acceptable in that emetic tolerance to xanthines does not occur and that a conditioned reflex to emesis is difficult to establish over such a short period (McColl et al., 1956). $ED_{50}$ values were calculated according to the method of Litchfield and Wilcoxon (1949).

2. Oral Minimum Emetic Dose

The minimum dose of each compound which causes emesis after oral administration was estimated in a group of five adult mongrel dogs of either sex. Logarithmically increasing or decreasing (depending upon response) doses of each compound were administered orally via a flexible stomach tube. The compounds were dissolved in distilled water in concentrations to allow a constant volume dose of 5 ml/kg. Animals were fasted overnight prior to dosing, were given a minimum of 3 days rest between doses, and did not receive the same compound twice in succession. Onset, frequency, and duration of emetic episodes as well as signs of CNS stimulation were also recorded.

F. Voluntary Motor Activity Studies in Mice

In an attempt to quantitatively assess central nervous system activity, each compound was evaluated for its influence on voluntary motor activity in mice according to the method described by Dews (British J. Pharmacol. 8:46, 1953). Three cylindrical actophotometer cages were utilized simultaneously, each with six light beams and six photoelectric cells. Individual digital counters were connected to each activity cage. Male albino Swiss mice with weights ranging between 19 and 24 gm were used throughout. Compounds were dissolved in distilled water and were injected intraperitoneally in logarithmically spaced doses to groups of five mice, three groups per dose level. Control groups received saline. Immediately after injection, the five mice were placed into the activity cage and the count was obtained for a 15 minute period.

G. Diuretic Studies

1. Acute Oral Evaluation in Rats

The oral diuretic effect of each compound was estimated in rats by a modification of the method described by Lipschitz et al. (J. Pharmacol. Exp. Ther. 79:97, 1943). Male Sprague Dawley rats (Carworth) weighing between 153 and 220 gms were fasted overnight. Groups of five animals each were administered three appropriate logarithmically spaced doses of each compound dissolved in saline in a constant volume dose of 25 ml/kg via an oral feeding needle. Controls received the same dose of only saline. The rats were then placed in individual metabolism cages and deprived of food and water for the remainder of the experiment. At the end of six hours, each rat was forced to expel urine in the bladder by pulling on the base of the tail. Parameters measured included urine volume, pH, and sodium and potassium excretion as measured by atomic absorption analysis. Six hour values were averaged for each dose of compound and for controls and were compared accordingly.

2. Acute Intravenous Evaluation in Dogs

The acute intravenous diuretic activity of three logarithmically divided doses of each compound was determined in adult female mongrel dogs by a method similar to that defined by Ross and Cafruny (J. Pharmacol. Exp. Ther. 140:125, 1963). Compounds were tested in two dogs each. Animals were initially hydrated with 30 ml/kg of water, orally; then anesthetized with pentobarbital sodium, 30–35 mg/kg i.v. One femoral vein was cannulated and a constant intravenous infusion of warm saline (3 ml/min.) was begun and continued throughout the experiment. The contralateral femoral vein was also cannulated for intravenous drug administration. Urine was directly collected from bilateral ureter cannulae. After a 20-minute control collection period, the first dose of the appropriate compound was injected and urine was collected at 20-minute intervals for a period of one hour. This procedure was repeated for two additional doses of the same compound. Urine volume, pH, and sodium and potassium levels were determined for each 20-minute collection period and sums were obtained for the one-hour period after each dose. Test results, reported as successive changes in each parameter, were compared accordingly.

RESULTS

Experimental results are summarized in Table I wherein pharmacologic and toxicologic activities relative to that of theophylline are expressed on a molar basis. Based on these data Table II estimates the actual dose of each compound that would be equivalent to the recommend therapeutic dose of theophylline and the degree of major side effects that would be produced by that particular dose.

TABLE I

| SUMMARY OF RELATIVE MOLAR ACTIVITIES | | | | | |
|---|---|---|---|---|---|
| Study | I | II | III | IV | V |
| | BRONCHODILATOR ACTIVITY | | | | |
| In-Vitro (Tracheal Strip) | 1.00 | 0.16 | 1.86 | 2.05 | 0.99 |
| In-Vivo I.P. (G. Pig) | 1.00 | 0.12 | 3.26 | 0.94 | 1.56 |
| In-Vivo, Oral (G.Pig) | 1.00 | 0.13 | 3.30 | 0.92 | 0.75 |
| Oral $LD_{50}{}^a$/Oral $PD_{50}{}^b$ (G. Pig) | 1.00 | 2.00 | 5.43 | 3.57 | 3.75 |
| Mean | 1.00 | 0.60 | 3.46 | 1.87 | 1.76 |
| | ACUTE TOXICITY AND SIDE EFFECT ACTIVITY | | | | |
| I.V. $LD_{50}$ (Mice) | 1.00 | 0.22 | 1.79 | 1.54 | 0.68 |
| Oral $LD_{50}$ (Mice) | 1.00 | 0.11 | 1.67 | 0.64 | 0.25 |
| Oral $LD_{50}$ (G. Pig) | 1.00 | 0.06 | 0.61 | 0.26 | 0.20 |
| Vadodilator, $HLPP^c$ (Dogs) | 1.00 | 0.06 | 0.76 | 1.06 | 0.40 |
| In-Vitro; MCF, HR, $CF^d$ (Rabbit Heart) | 1.00 | $e$ | 1.40 | 1.81 | 0.93 |
| I.V. Cardiovascular (Dogs)$^f$ | 1.00 | 0.36 | 1.16 | 2.02 | 0.91 |
| Oral Emetic (Dogs) | 1.00 | <0.50 | 251.00 | 6.00 | 0.50 |
| I.V. Emetic (Dogs) | 1.00 | 0.09 | 134.17 | 12.88 | 1.91 |
| Oral Diuretic (Rats) | 1.00 | 0.71 | 7.29 | 1.48 | 1.05 |
| I.V. Diuretic (Dogs) | 1.00 | 0.26 | 0.50 | 0.45 | 0.59 |
| I.P. CNS Stimulation (Mice) | 1.00 | 0.18 | 1.73 | 0.48 | 0.30 |
| Mean | 1.00 | 0.26 | 36.55 | 2.60 | 0.70 |
| Therapeutic Efficacy$^g$ | 1.00 | 2.31 | 0.09 | 0.72 | 2.51 |
| Water Solubility % (W/V) | 0.8 | 33.0 | 1.0 | 3.0 | 10.0 |

I - Theophyline
II - Dyphylline
III - 7-(2-Hydroxypropyl)-1,3-di-n-propylxanthine
IV - 7-(3-Hydroxypropyl)-1,3-di-n-propylxanthine
V - 7-2,3-dihydroxypropyl)-1,3-di-n-propylxanthine
$a$ - Oral $LD_{50}$: Median lethal dose.
$b$ - Oral $PD_{50}$: Median protective dose.
$c$ - HLPP: Hind limb perfusion preparation.
$d$ - Mean relative activity for MCF, myocardial contractile force; HR, heart rate; CF, coronary flow.
$e$ - Dyphylline not tested in this experiment.
$f$ - Mean relative activity for effects on arterial pressure, heart rate, contractile force, cardiac output, stroke volume, cardiac work, total peripheral resistance, coronary flow, and coronary resistance.
$g$ - Mean bronchodilator (therapeutic) activity divided by mean acute toxic and side effect activity.

TABLE II

| ESTIMATED PHARMACOLOGIC EFFECTS AT EQUIVALENT THERAPEUTIC DOSES | | | | | |
|---|---|---|---|---|---|
| | I | II | III | IV | V |
| Estimated Human Bronchodilator Dose$^a$ (HBD):(mg/70 kg.) | 200 | 2353 | 99 | 347 | 299 |
| (mg/kg.) | 2.9 | 33.6 | 1.4 | 5.0 | 4.3 |
| Would cause the following effects: Cardiovascular: (I.V. dogs) | | | | | |
| $MAP^b$ (ΔmmHg) | −12 | −20 | −8 | −25 | −5 |
| Hr (ΔBPM) | +11 | +11 | +21 | +80 | +7 |
| MCF (%Δ) | +17 | −5 | +28 | +20 | +15 |
| CO (%Δ) | +7 | −15 | +10 | +2 | +6 |
| CW (%Δ) | −5 | −30 | +2 | −26 | +2 |

TABLE II-continued

| ESTIMATED PHARMACOLOGIC EFFECTS AT EQUIVALENT THERAPEUTIC DOSES | | | | | |
|---|---|---|---|---|---|
| | I | II | III | IV | V |
| TPR (%Δ) | −12 | +3 | −15 | −5 | −9 |
| CF (%Δ) | +21 | +10 | +8 | +4 | +17 |
| (Mean) | (12) | (13) | (13) | (23) | (9) |
| Emetic:[c] | | | | | |
| I.V. Dogs | None | None | Severe | Moderate | None |
| (ED$_{50}$mg/kg.) | (58) | (900) | (0.7) | (7.5) | (53) |
| P.O. Dogs | None | None | Severe | None | None |
| (MED mg/kg.) | (128) | (>362) | (0.8) | (33) | (442) |
| CNS Activity: | | | | | |
| I.P. Mice | Moderate | | Severe | Moderate | None |
| (%Δ) | (+23) | —[d] | (−60) | (−17) | (−1) |
| Diuretic Activity: | | | | | |
| I.V. Dogs | Mild | Moderate | Mild | Mild | Mild |

I - Theophylline
II - Dyphylline
III - 7-(2-Hydroxypropyl)-1,3-di-n-propylxanthine
IV - 7-(3-Hydroxypropyl)-2,3-di-n-propylxanthine
V - 7-(2,3-dihydroxypropyl)-1,3-di-n-propylxanthine
[a] - Dose: Based on the recommended dose for theophylline and the relative activities in the bronchodilator experiments.
[b] - MAP: Mean arterial pressure; HR: heart rate; MCF: myocardial contractile force, CO: cardiac output; CW: cardiac work; TPR: total peripheral resistance; CF: coronary flow.
[c] - ED$_{50}$: median emetic dose, MED: minimum emetic dose.
[d] - unable to estimate.

Therapeutically effective bronchodilator, i.e., bronchial muscle relaxant, quantities of 7-(2,3-dihydroxypropyl)-1,3-di-n-propylxanthine may be administered to a living animal body suffering from reversible airway obstruction due to bronchoconstriction by any suitable means and in any suitable form. Also, effective quantities of 7-(2,3-dihydroxypropyl)-1,3-di-n-propylxanthine can be incorporated into a pharmaceutical composition of the form customarily employed for oral and parenteral administration and administered to a living animal body. Pharmaceutical compositions for oral administration containing the compound can be in liquid form, such as solutions, suspensions or syrups or in solid form, for example, tablets, capsules, or powders. Those compositions for parenteral administration can be in the form of sterile aqueous solutions or suspensions. Advantageously the pharmaceutical composition containing the compound can be prepared in unit dosage form using pharmaceutically acceptable carriers such as starch, glucose, lactose, gelatin, sucrose, stearates, phosphates, water for injection and the like. Buffers and preservatives as well as other pharmaceutical medicaments may be present.

The amount of 7-(2,3-dihydroxypropyl)-1,3-di-n-propylxanthine administered to the living animal body will, of course, vary depending among other things on the size of the living animal body, the particular animal body to be treated, the seriousness of the reversible airway obstruction due to bronchoconstriction, and the general health of the living animal body. Any pharmaceutically effective amount may be employed which is sufficient to relax the bronchial muscle and thereby relieve or partially relieve the airway obstruction. The dosage can be determined with regard to established medical practice. Generally, the amount of 7-(2,3-dihydroxypropyl)-1,3-di-n-propylxanthine administered is equal to about 1.0 mg. to about 10.0 mg. per kg. of animal body weight. Preferably the amount administered will be in the range of from about 3.0 mg. to 7.0 mg. per kg. of animal body weight.

As various changes could be made in the above methods and products without departing from the scope of the invention, it is intended that all matter contained in the above description shall be interpreted as illustrative. It is to be understood therefore that the invention is not limited except as defined by the appended claims.

What is claimed is:

1. The compound 7-(2,3-dihydroxypropyl)-1,3-di-n-propylxanthine.

2. A method for the treatment of reversible airway obstruction due to bronchoconstriction in a living animal body which comprises administering to a living animal body suffering from said obstruction a therapeutically effective amount of the compound of claim 1.

3. A pharmaceutical composition comprising a pharmaceutically acceptable carrier and a therapeutically effective bronchodilater amount of the compound of claim 1.

* * * * *